United States Patent
Merschon et al.

(10) Patent No.: US 9,265,434 B2
(45) Date of Patent: Feb. 23, 2016

(54) DYNAMIC FEATURE RICH ANATOMICAL RECONSTRUCTION FROM A POINT CLOUD

(71) Applicant: BIOSENSE WEBSTER (ISRAEL) LTD., Yokneam (IL)

(72) Inventors: Asaf Merschon, Karkur (IL); Fady Massarwa, Baka El Gharbiya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 36 days.

(21) Appl. No.: 14/132,631

(22) Filed: Dec. 18, 2013

(65) Prior Publication Data
US 2015/0164356 A1   Jun. 18, 2015

(51) Int. Cl.
| A61B 5/04 | (2006.01) |
|---|---|
| A61B 5/044 | (2006.01) |
| A61B 5/042 | (2006.01) |
| A61B 5/00 | (2006.01) |
| A61B 5/0402 | (2006.01) |
| A61B 5/103 | (2006.01) |

(52) U.S. Cl.
CPC ........... *A61B 5/04017* (2013.01); *A61B 5/0044* (2013.01); *A61B 5/0402* (2013.01); *A61B 5/042* (2013.01); *A61B 5/044* (2013.01); *A61B 5/103* (2013.01); *A61B 5/6852* (2013.01); *A61B 5/6869* (2013.01)

(58) Field of Classification Search
None
See application file for complete search history.

(56) References Cited

U.S. PATENT DOCUMENTS

| 6,226,542 | B1 | 5/2001 | Reisfeld | |
|---|---|---|---|---|
| 6,301,496 | B1 | 10/2001 | Reisfeld | |
| 6,814,733 | B2 | 11/2004 | Schwartz | |
| 6,892,091 | B1 | 5/2005 | Ben-Haim | |
| 6,997,924 | B2 | 2/2006 | Schwartz | |
| 7,156,816 | B2 | 1/2007 | Schwartz | |
| 7,263,397 | B2 * | 8/2007 | Hauck et al. | 600/374 |
| 7,505,810 | B2 * | 3/2009 | Harlev et al. | 600/509 |
| 7,536,218 | B2 | 5/2009 | Govari | |
| 7,756,576 | B2 | 7/2010 | Levin | |
| 8,041,413 | B2 * | 10/2011 | Barbagli et al. | 600/424 |
| 2007/0270705 | A1 * | 11/2007 | Starks | 600/523 |
| 2007/0299352 | A1 | 12/2007 | Harlev et al. | |
| 2008/0009758 | A1 * | 1/2008 | Voth | 600/523 |
| 2009/0171627 | A1 * | 7/2009 | Olson | 703/1 |
| 2010/0063784 | A1 | 3/2010 | Chang | |
| 2010/0067755 | A1 * | 3/2010 | Chan et al. | 382/128 |
| 2010/0274123 | A1 | 10/2010 | Voth | |
| 2011/0152684 | A1 * | 6/2011 | Altmann et al. | 600/443 |
| 2013/0173222 | A1 * | 7/2013 | Voth | 703/1 |

OTHER PUBLICATIONS

U.S. Appl. No. 13/669,511, filed Nov. 6, 2012.
Attene et al. Mesh Segmentation—A Comparative Study. In Proceedings of Shape Modelling International (SMI'06), IEEE Computer Society Press, pp. 14-25, 2006.

(Continued)

*Primary Examiner* — Brian T Gedeon
(74) *Attorney, Agent, or Firm* — Louis J. Capezzuto (57) ABSTRACT

3-dimensional cardiac reconstruction is carried out by catheterizing a heart using a probe with a mapping electrode, and acquiring electrical data from respective locations in regions of interest in the heart, representing the locations of the electrical data as a point cloud, reconstructing a model of the heart from the point cloud, applying a set of filters to the model to produce a filtered volume, segmenting the filtered volume to define components of the heart, and reporting the segmented filtered volume.

14 Claims, 4 Drawing Sheets

(56) References Cited

OTHER PUBLICATIONS

Au et al. Skeleton Extraction. ACM Trans. Graph., 2008, vol. 27, 3, Article No. 44.

Katz et al. Mesh Segmentation Using Feature Point and Core Extraction. Visual Comput, 2005, DOI 10.1007/s00371-005-0344-9.

Meyer et al. Discrete Differential-Geometry Operators for Triangulated 2-Manifolds. Visualization and Mathematics III Mathematics and Visualization 2003, pp. 35-57.

European Search Report dated May 22, 2015 for Application No. EP14198635.

* cited by examiner

DYNAMIC FEATURE RICH ANATOMICAL RECONSTRUCTION FROM A POINT CLOUD

BACKGROUND OF THE INVENTION

1. Field of the Invention

This invention relates to medical imaging. More particularly, this invention relates to reconstruction of an anatomic structure from relatively sparse data.

2. Description of the Related Art

Medical catheterizations are routinely carried out today, for example, in cases of cardiac arrhythmias, such as atrial fibrillation, which occur when regions of cardiac tissue abnormally conduct electric signals to adjacent tissue, thereby disrupting the normal cardiac cycle and causing asynchronous rhythm. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions. It is desirable in such procedures to provide a convenient representations of the cardiac anatomy to the operator.

For example, the left atrium is a complicated 3-dimensional structure, the walls of which have dimensions, which differ from person to person, although all left atria have the same underlying shape. The left atrium can be divided into a number of substructures, such as the pulmonary vein, the mitral or bicuspid valve and the septum, which are conceptually easy to identify. The sub-structures also typically differ from person to person, but as for the overall left atrium, each substructure has the same underlying shape. In addition, a given substructure has the same relationship to the other substructures of the heart, regardless of the individual differences in shapes of the substructures.

SUMMARY OF THE INVENTION

A collection of sparse data, known as a "point cloud", typically associated with a coordinate system, may be produced by imaging systems during a medical catheterization. Disclosed herein are methods and systems for developing a feature-rich 3-dimensional reconstruction of an anatomic structure from a point cloud, e.g., a point cloud obtained from a heart or portion thereof. The point cloud may be relatively sparse.

When using a point cloud to reconstruct a 3D model of the heart, there is a question of an appropriate resolution of the reconstruction. A low resolution gives a rough reconstruction but works well with low-density point clouds. A high resolution gives a much more feature rich reconstruction, but is more prone to errors when applied to low density point clouds (holes and disconnected floating elements). This can be overcome by manually setting separate resolutions for separate regions of the reconstruction. However, the manual process is uncomfortable and takes some time. An automatic approach is preferable.

There is provided according to embodiments of the invention a method of 3-dimensional cardiac reconstruction, which is carried out by inserting a probe into a heart of a living subject, the probe has a mapping electrode, urging the mapping electrode into contacting relationships with a tissue in plurality of regions of interest of the heart, acquiring electrical data from respective locations in the regions of interest, representing the locations of the electrical data as a point cloud, reconstructing a model of the heart from the point cloud, applying a set of filters to the model to produce a filtered volume, segmenting the filtered volume to define components of the heart, and reporting the segmented filtered volume, wherein at least one of the above steps is implemented in computer hardware or computer software embodied in a non-transitory computer-readable storage medium.

In an aspect of the method, reconstructing a model and applying a set of filters are performed iteratively using portions of the point cloud until a stop condition is met. The stop condition may include one of a failure to achieve a progressively higher resolution of the filtered volume in a predetermined number of iterations, an expiration of a preset time interval and a completion of a predetermined number of iterations.

According to an additional aspect of the method, applying a set of filters includes applying respective subsets of the set of filters in successive iterations thereof.

According to yet another aspect of the method, the subsets are chosen randomly.

According to still another aspect of the method, the subsets are chosen according to a search strategy.

According to a further aspect of the method, applying a set of filters includes making a determination that the filtered volume has a resolution that exceeds a resolution of the filtered volume of a preceding iteration of applying a set of filters, and responsively to the determination, using the filtered volume as an input to a subsequent iteration of reconstructing a model and applying a set of filters.

A further aspect of the method is carried out after segmenting the filtered volume by storing respective instances of the segmented filtered volume, and combining the instances of the segmented filtered volume into a composite volume, and displaying the composite volume.

There is further provided according to embodiments of the invention an apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
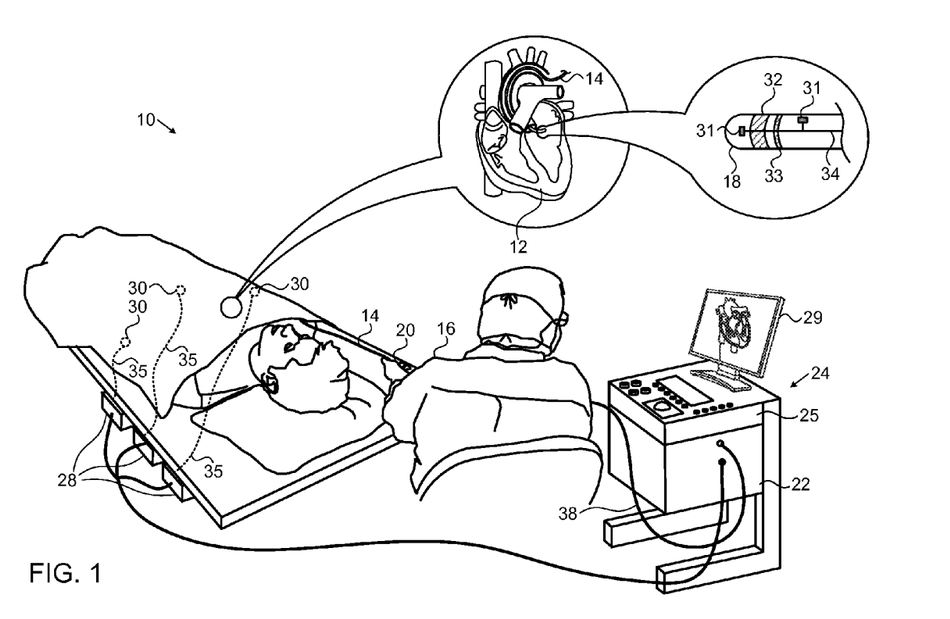
FIG. 1 is a pictorial illustration of a system for catheterizing a heart of a living subject, which is constructed and operative in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with an embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24, are disposed between the ablation electrodes 32 and have connections to the cable 34.

Wire connections 35 link the console 24 with body surface electrodes 30 and other components of a positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor such as thermocouples 31, may be mounted on or near the ablation electrode 32 and optionally or near the sensing electrode 33.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The processor 22 functions as an element of a positioning subsystem in the system 10 that measures location and orientation coordinates of the catheter 14. The processor 22 has additional image processing functions, which are described in further detail hereinbelow.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
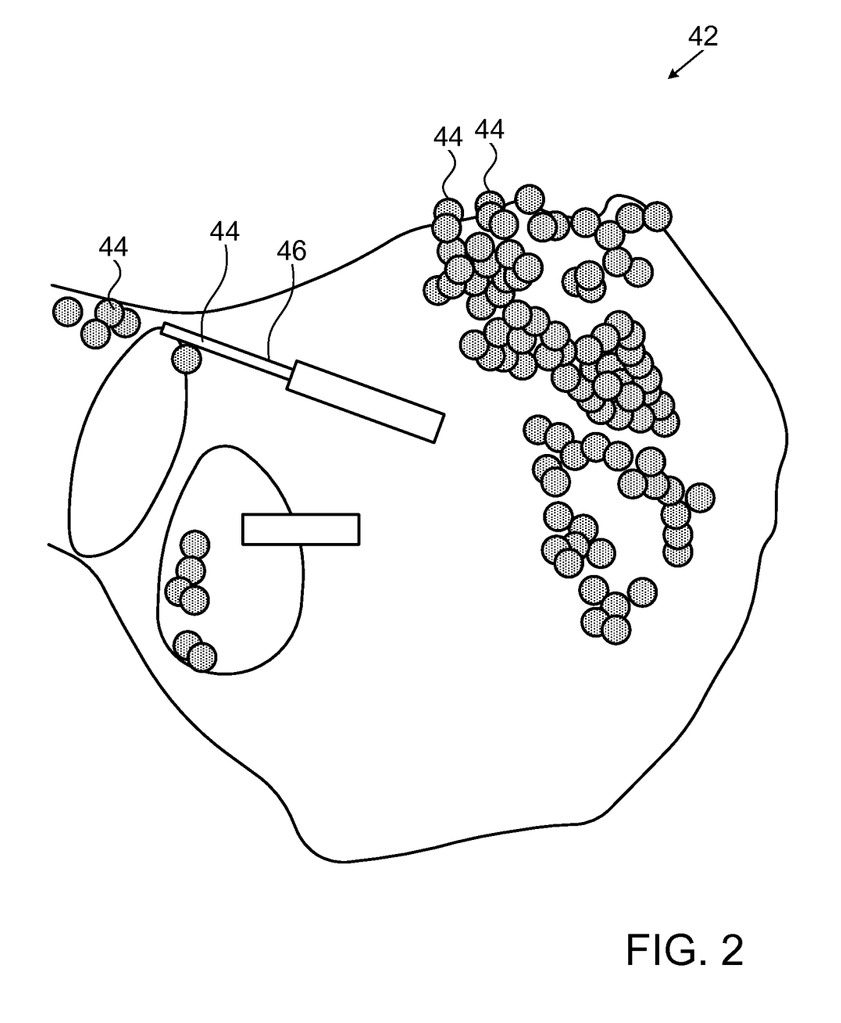
FIG. 2 is an illustration of a sparse point cloud aofl cardiac data obtained from respective locations in accordance with an embodiment of the invention.

Reference is now made to FIG. 2, which is an illustration of a sparse point cloud 42 of cardiac data obtained from respective locations in accordance with an embodiment of the invention. Such a point cloud may be acquired by ultrasound imaging of a chamber of a heart. Alternatively, the locations of data 44 are reported by a location sensor on the catheter, as known in the art. For example, sparse data may be acquired using the fast anatomic mapping (FAM) functions of the CARTO® 3 System cooperatively with a mapping catheter such as the Navistar® Thermocool® catheter, both available from Biosense Webster, Inc., 3333 Diamond Canyon Road, Diamond Bar, Calif. 91765. Processors such as are found in the CARTO system may be programmed to carry out the functions described below by those skilled in the art.

The data 44 may be associated with respective coordinates in a 3-dimensional space, based on anatomic landmarks or fiducial marks, using location information provided by location sensors 46 on a catheter 48 as shown in FIG. 2. The location information may be described with 6 degrees of freedom.

Figure 3:
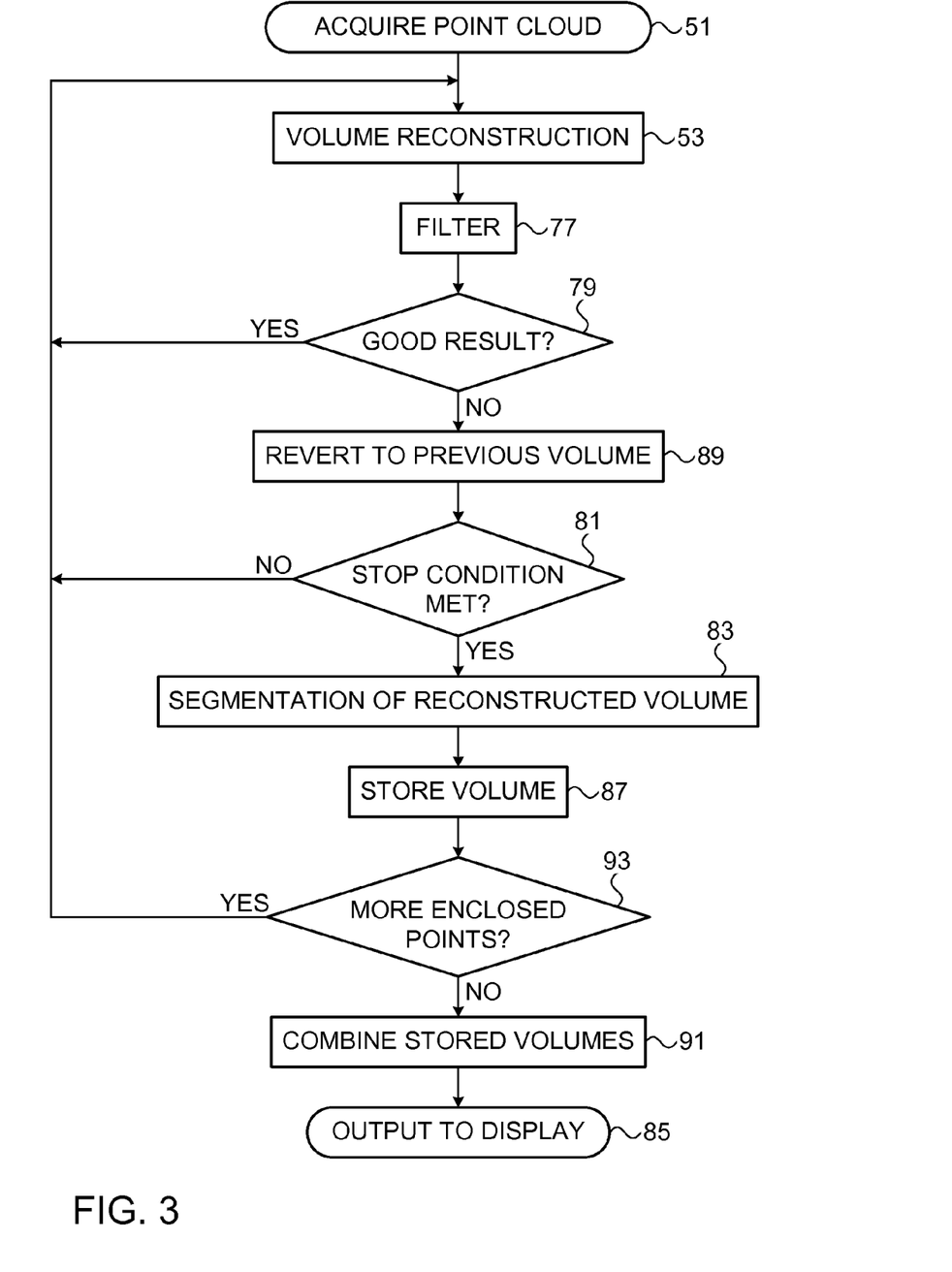
FIG. 3 is a flow chart of a method for 3-dimensional anatomical reconstruction from a point cloud, in accordance with an embodiment of the invention.

Reference is now made to FIG. 3, which is a flow chart of a method for 3-dimensional anatomical reconstruction from a point cloud, in accordance with an embodiment of the invention. At initial step 51, a point cloud of a structure, e.g., the point cloud 42 (FIG. 3) of a heart or portion thereof is acquired as described above, using the facilities of the system 10 (FIG. 1) or an equivalent system.

Next, at step 53 an initial volume reconstruction is prepared from the point cloud that was obtained in initial step 51. It should be noted that initial step 51 and step 53 may be performed in the same or different catheterization sessions. One way of performing step 53 is associating data 44 with the center of a corresponding volume element or voxel (not shown) and performing the process steps described below.

Figure 4:
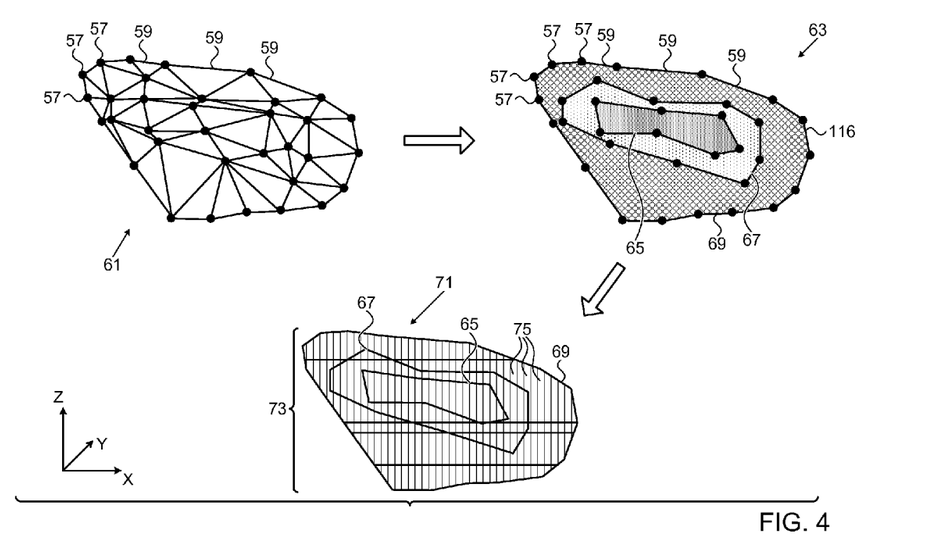
FIG. 4 is a series of diagrams illustrating stages in a volume reconstruction from a point cloud, in accordance with an embodiment of the invention.

Reference is now made to FIG. 4, which is a series of diagrams illustrating stages in a volume reconstruction from a point cloud, in accordance with an embodiment of the invention. The processor 22 (FIG. 1) uses a mapping module to initially connect locations 57 of the point cloud, e.g., data 44 (FIG. 3) to define a mesh 61 of line segments 59, The mesh 61 typically, although not necessarily, is a triangular mesh. In one embodiment, the processor 22 uses the Ball-Pivoting Algorithm (BPA) to produce the mesh 61. Typically, if the BPA is used, a size of the ball is set to correspond to the size of the voxels referred to above. Alternatively, the mesh 61 may be generated as a Delaunay triangulation, comprising a plurality of triangles having vertices corresponding to the locations 57. The triangles of the triangulation may be based on Voronoi diagrams formed about the locations 57. However, the processor 22 may use any convenient method that is known in the art for forming a mesh.

After producing the mesh 61, the processor 22 generates a generally smooth surface 63 connecting locations 57 and line segments 59. To generate the surface 63, the processor 22 typically uses interpolation and additionally or alternatively extrapolation. In addition, to ensure that the surface 63 is generally smooth, the processor 22 may adjust the surface to be close to, but not necessarily include, some of the locations 57 and line segments 59. By way of example, the surface 63 has contours 65, 67, 69.

Then, after generating surface 63, the processor 22 checks if the surface is closed, i.e., if the surface is topologically equivalent to a closed surface such as a sphere. Typically, surface 63 is not closed, having one or more openings. The openings in surface 108 may represent structures that naturally occur in the organ, such as the superior vena cava, or the inferior vena cava of the right atrium. Such openings are herein referred to as natural openings. Additionally, there may be openings in surface 63, herein referred to as artificial openings, because the organ has not been fully mapped.

In the event that surface 63 is not closed, the processor 22 closes the surface by adding further surface elements until the surface is closed. The surface produced by closing surface 63 is herein referred to as closed surface 71. In one embodiment, an opening is closed by adding an oriented bounding box that surrounds the opening, the box having a minimal volume. The box is then treated as part of the surface.

The closed surface 71 is assumed to have a defining equation:

$$S_1(x,y,z)=0 \qquad \text{Eq. (1),}$$

where $S_1$ is a function. The closed surface 71 encloses a volume 73 comprising voxels 75. Volume 73 is also referred to herein as volume $V_1$, which may be defined as follows:

$$V_1=\{V(x,y,z)|S_1(x,y,z)<0\} \qquad \text{Eq. (2),}$$

where $V(x, y, z)$ represents a voxel centered on $(x, y, z)$, and $V_1$ is the volume formed by the voxels 75.

Returning to FIG. 3, the process continues with step 77. The volume 73 (FIG. 4) is subjected to a set of filter functions F. Some of the filter functions F may be applied to the mesh 61 and others to the volume 73. An exemplary list of filter functions follows:

f1: Given a mesh, calculate a mesh genus G, according to Euler's Graph invariant characteristic χ, which is well known in the field of algebraic topology, and return whether G==1. If not, there is a hole in the mesh.

f2: Given a mesh, find how many (n) well-connected elements there are and return whether n==1. If not the mesh is composed of at least two separated elements. This is inconsistent with an anatomic structure, which would correspond to a mesh having one element, i.e., a single connected mesh.

f3: Given a mesh find the vertices with the maximal discrete Gaussian curvature K in the reconstructed mesh. The Gaussian curvature K may be computed using the Gaussian curvature operator $$\kappa_G(x_i) = \left(2\pi - \sum_{j=1}^{\#f} \theta_j / A_{Mixed}\right)$$

where $\theta_j$ is the angle of the $j^{th}$ face at the vertex $x_i$, and #f denotes the number of faces around the vertex $x_i$. $A_{Mixed}$ is the mixed area in the mesh about the vertex $x_i$.

The discrete Gaussian curvature K is described in the publication *Discrete Differential-Geometry Operators for Triangulated 2-Manifolds*, Mark Meyer et al., International Workshop on Visualization and Mathematics (2002), which is herein incorporated by reference.

Then determine whether max delta K is less than a specified threshold, wherein delta K refers to changes in the Gaussian curvature K in successive mesh segmentations. This gives an indication of the smoothness of the mesh.

f4: For a given mesh compute its skeleton, and check to see if it is without junctions. The presence of junctions indicates that a mesh has appendages, and so needs further iterations of segmentation. Methods for building a mesh skeleton graph are known, for example, from the document *Skeleton Extraction by Mesh Contraction*, Oscar Kin-Chung Au et al., ACM Trans. on Graph, vol. 27, no. 3, pp. 44:1-44:10, 2008.

f5: Run the segmentation algorithms S that are tube oriented (in order to find cylindrical elements), and see if the number of elements is equal or greater or equal to a specified number. Hierarchical body segmentation algorithms are suitable for example, as taught in the document *Mesh Segmentation Using Feature Point and Core Extraction*, Sagi Katz et al., The Visual Computer, Vol. 21, No. 8-10. (September 2005), pp. 649-658, which is herein incorporated by reference.

Preferably, all the filters F should be used. However, in some applications subsets of the filters F may be sufficient, and are economical of computer resources. Various subsets of the filters F may be chosen in different iterations of step 77. The subsets may be chosen according to an empirically developed order in order to most rapidly improve the mesh in various cardiac applications. Alternatively, the subsets may be chosen randomly or directed by the operator. Further alternatively, the set of filters F may be treated as a search space and the subsets can be selected according to search strategies, and methods known in the art of optimization. For example, the subsets could be chosen in the following order: {f1, f2, f3, f5}, {f1, f2, f3}, {f1, f2, f5}, {f1, f2}, {f1, f2, f3, f4, f5}, {f1, f2, f3, f4}, {f1, f2, f4, f5}, and {f1, f2, f4}. The choice of sets may be automatically established in any given iteration according to progress made in previous iterations of step 77. In general, the quality of the results correlates with the number of filters used.

Next, at decision step 79, it is determined whether the mesh at its current resolution is a "good mesh", i.e., (1) the mesh meets some predetermined criterion or has a predetermined quality, and (2) the current mesh has a higher resolution than in the last iteration.

Each of the filters F has its own figure of merit, indicating the quality of the result. The criteria to be applied in evaluating the results of the filters are application dependent, and is accordingly selected by the user. For example, a combined figure of merit may be developed. Alternatively, the results of a minimum set of the filters F should meet or exceed their respective criteria. Many combinations of respective criteria for the filters F may be established. Regarding the Gaussian curvature, a choice of values between 2*PI and 1.5*PI is typical. In another example, for the Genus value filter (Euler's method), a choice of 0 is typical.

Generally, the quality of the results correlates with the number of filters employed.

If the determination at decision step 79 is affirmative, then, in order to attempt to obtain an even better resolution control returns to step 53, which is performed referring to a subset of the raw point cloud that is associated with the segmented portion currently in progress, to reconstruct a volume and iterate the filtering operations described above. Optionally, additional interpolated points on the surface 63 may be included among the locations 57.

If the determination at decision step 79 is negative, then at step 89 the current reconstructed value is discarded, and the method continues, using the result of the previous iteration.

Control next proceeds to decision step 81, where it is determined if a stop condition has been met. If not, then control returns to step 53 in order to improve the quality of the current reconstructed volume. Typical stop conditions include failure to progress in a predetermined number of iterations, expiration of a preset time interval or completion of a predetermined number of iterations.

If a stop condition has not been met in decision step 81, then segmentation of the reconstructed volume is performed in step 83. The segmentation algorithm does not require operator interaction to identify segments of the heart. The Plumber algorithm involving shape segmentation into tubular parts is suitable for use in step 83. This algorithm is described in the document *Mesh segmentation—A Comparative Study*, M. Attene et al., Proceedings of the IEEE International Conference on Shape Modeling and Applications 2006, which is herein incorporated by reference. Other segmentation algorithms known in the art may also be used.

The current segmented volume represents the best result attained thus far. It is stored at step 87.

At decision step 93, it is determined if enclosed points remain to be processed. If the determination is affirmative, then control returns to step 53. It is desirable to iterate the steps beginning with step 53 using different enclosed points in the mesh and corresponding portions of the raw point cloud (rather than the entire point cloud as in the first iteration).

If the determination at decision step 93 is negative, then control proceeds to step 91. The volumes stored in step 87 are now combined into a single composite mesh. This step may be accomplished using the teachings of commonly assigned application Ser. No. 13/669,511, entitled "Combining Three-Dimensional Surfaces", whose disclosure is herein incorporated by reference. The combined surface provides a more complete 3-dimensional model than any of the individual meshes, without loss of accuracy.

Upon completion of step 91, the composite mesh is output to a display at final step 85.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
inserting a probe into a heart of a living subject, the probe having a mapping electrode;
urging the mapping electrode into contacting relationships with a tissue in plurality of regions of interest of the heart;
acquiring electrical data from respective locations in the regions of interest;
representing the locations of the electrical data as a point cloud;
reconstructing a model of the heart from the point cloud;
applying a set of filters to the model to produce a filtered volume, wherein the steps of reconstructing the model and applying the set of filters are performed iteratively using portions of the point cloud until a stop condition is met;
segmenting the filtered volume to define components of the heart; and
reporting the segmented filtered volume, wherein at least one of the above steps is implemented in computer hardware or computer software embodied in a non-transitory computer-readable storage medium.

2. The method according to claim 1, wherein applying a set of filters comprises applying respective subsets of the set of filters in successive iterations thereof.

3. The method according to claim 2, wherein the subsets are chosen randomly.

4. The method according to claim 2, wherein the subsets are chosen according to a search strategy.

5. The method according to claim 1, wherein the stop condition comprises one of a failure to achieve a progressively higher resolution of the filtered volume in a predetermined number of iterations, an expiration of a preset time interval and a completion of a predetermined number of iterations.

6. The method according to claim 1, wherein applying a set of filters comprises:
making a determination that the filtered volume has a resolution that exceeds a resolution of the filtered volume of a preceding iteration of applying a set of filters; and
responsively to the determination, using the filtered volume as an input to a subsequent iteration of the steps of reconstructing a model and applying a set of filters.

7. The method according to claim 6, further comprising the steps of:
after performances of the step of segmenting the filtered volume storing respective instances of the segmented filtered volume; and combining the instances of the segmented filtered volume into a composite volume, wherein displaying the segmented filtered volume comprises displaying the composite volume.

8. An apparatus, comprising:

a probe adapted for insertion into contact with a heart in a body of a subject, the probe having a location sensor and an electrode on a distal portion of the probe;

a processor linked to the location sensor, and operative performing the steps of:

accepting electrical data from the electrode when the probe is in respective locations in regions of interest in the heart;

representing the locations of the electrical data as a point cloud;

reconstructing a model of the heart from the point cloud;

applying a set of filters to the model to produce a filtered volume, wherein the steps of reconstructing the model and applying the set of filters are performed iteratively using portions of the point cloud until a stop condition is met;

segmenting the filtered volume to define components of the heart; and reporting the segmented filtered volume.

9. The apparatus according to claim 8, wherein applying a set of filters comprises applying respective subsets of the set of filters in successive iterations thereof.

10. The apparatus according to claim 9, wherein the subsets are chosen randomly.

11. The apparatus according to claim 9, wherein the subsets are chosen according to a search strategy.

12. The apparatus according to claim 8, wherein the stop condition comprises one of a failure to achieve a progressively higher resolution of the filtered volume in a predetermined number of iterations, an expiration of a preset time interval and a completion of a predetermined number of iterations.

13. The apparatus according to claim 8, wherein applying a set of filters comprises:

making a determination that the filtered volume has a resolution that exceeds a resolution of the filtered volume of a preceding iteration of applying a set of filters; and responsively to the determination, using the filtered volume as an input to a subsequent iteration of the steps of reconstructing a model and applying a set of filters.

14. The apparatus according to claim 13, further comprising a display, wherein the processor is operative to perform the additional steps of:

after performances of the step of segmenting the filtered volume storing respective instances of the segmented filtered volume; and combining the instances of the segmented filtered volume into a composite volume, wherein reporting the segmented filtered volume comprises presenting the composite volume on the display.

* * * * *